US008771611B2

(12) United States Patent
Hong et al.

(10) Patent No.: US 8,771,611 B2
(45) Date of Patent: Jul. 8, 2014

(54) SYSTEM AND METHODS OF LOG-SCALE CONCENTRATION GRADIENTS

(75) Inventors: Jong Wook Hong, Auburn, AL (US); Se-Kwon Kim, Pusan (KR); Jae Young Yun, Seoul (KR)

(73) Assignees: Auburn University, Auburn, AL (US); Pukyong National University, Pusan (KR)

( * ) Notice: Subject to any disclaimer, the term of this patent is extended or adjusted under 35 U.S.C. 154(b) by 0 days.

(21) Appl. No.: 13/305,645

(22) Filed: Nov. 28, 2011

(65) Prior Publication Data

US 2013/0164770 A1 Jun. 27, 2013

(51) Int. Cl.
*G01N 15/06* (2006.01)

(52) U.S. Cl.
USPC ............ 422/503; 422/68.1; 422/81; 422/502; 436/43; 436/180

(58) Field of Classification Search
USPC ...................... 422/68.1, 81, 502, 503; 436/43
See application file for complete search history.

(56) References Cited

U.S. PATENT DOCUMENTS

| | | | |
|---|---|---|---|
| 7,556,776 | B2 | 7/2009 | Fraden et al. |
| 2005/0172476 | A1 | 8/2005 | Stone et al. |
| 2006/0073035 | A1 | 4/2006 | Sundararajan |
| 2007/0006926 | A1 | 1/2007 | Prakash et al. |
| 2008/0166720 | A1 | 7/2008 | Hsieh et al. |
| 2009/0075390 | A1 | 3/2009 | Linder et al. |
| 2009/0302244 | A1 | 12/2009 | Wedel |
| 2011/0103176 | A1 | 5/2011 | Van Dam et al. |
| 2011/0151578 | A1 | 6/2011 | Abate et al. |

FOREIGN PATENT DOCUMENTS

WO 2009139898 A2 11/2009

OTHER PUBLICATIONS

Lee et al., "Predictive model on micro droplet generation through mechanical cutting" Microfluid Nanofluid, 2009, 7:431-438.
Copeland, R.A. "Mechanistic considerations in high-throughput screening" Analytical Biochemistry, 2003, 320:1-12.
Cortes et al "Relationships between inhibition constants, inhibitor concentrations for 50% inhibition and types of inhibition: new ways of analysing data" Biochem J., 2001, 357:263-268.
Rozman et al., "A Toxicologist's View of Cancer Risk Assessment", Drug Metabolism Reviews, 28(1&2), 29-52, 1996.
Waddell, W.J., "Thermodynamic basis for expressing dose logarithmically" Toxicology and Applied Pharmacology 2008, 228:156-157.
Seefeldt et al., "Log-Logistic Analysis of Herbicide Dose-Response Relationships" Weed Technology, 1995, vol. 9:218-227.
Kerby et al., "A fluorogenic assay using pressure-driven flow on a microchip", Electrophoresis, 2001, 22:3916-3923.
Song et al., "Millisecond Kinetics on a Microfluidic Chip Using Nanoliters of Reagents" J. Am. Chem. Soc. 2003, 125:14613-14619.

(Continued)

*Primary Examiner* — Brian J Sines
(74) *Attorney, Agent, or Firm* — Haverstock & Owens LLP

(57) ABSTRACT

Devices and methods use an integrated microfluidic system that has the capability of realizing a wide range of accurate dilutions in a logarithmic way through semi-direct dilution of samples inside a chip. The device for dose response analysis is able to contain a first fluid source on a microfluidic chip, wherein the first fluid source comprises a drug, a second fluid source on the microfluidic chip, a mixing area on the microfluidic chip fluidically coupling with the first and the second fluidic source, and a detection area coupling with the mixing area for drug information detection using a detection system.

16 Claims, 8 Drawing Sheets

(56) References Cited

OTHER PUBLICATIONS

Duffy et al., "Microfabricated Centrifugal Microfluidic Systems: Characterization and Multiple Enzymatic Assays" Analytical Chemistry, vol. 71, No. 20, Oct. 15, 1999, pp. 4669-4678.

Miller et al., "A Digital Microfluidic Approach to Homogeneous Enzyme Assays", Anal. Chem, 2008, 80, 1614-1619.

Kang et al., "Development of a microplate reader compatible microfluidic device for enzyme assay" Sensors and Actuators B 107 (2005) 980-985.

Hadd et al., "Microchip Device for Performing Enzyme Assays" Anal. Chem. 1997, 69:3407-3412.

Jambovane et al., "Creation of Stepwise Concentration Gradient in Picoliter Droplets for Parallel Reactions of Matrix Metalloproteinase II and IX" Anal. Chem. 2011, 83:3358-3364.

Thorsen et al., "Dynamic Pattern Formation in a Vesicle-Generating Microfluidic Device", Physical Review Letters, 2001, vol. 86, No. 18, 4163-4166.

Bui et al., "Enzyme Kinetic Measurements Using a Droplet-Based Microfluidic System with a Concentration Gradient" Anal. Chem., 2011, 83:1603-1608.

Quintero et al., "Quality Control Procedures for Dose-Response Curve Generation Using Nanoliter Dispense Technologies" J. Biomolecular Screening, 2007, 12(6), pp. 891-899.

Masse et al., "Compound Transfer to 3456-well Assay Plates Using the Echo™ 550." This is a reformatted version of a poster presented at the Society for Biomolecular Screening, Sep. 2005, Orlando, Florida.

Ellson et al., "Transfer of Low Nanoliter volumes between Microplates Using Focused Acoustics-Automation Considerations" JALA, 2003, 8:29-34.

Dunn et al., "Challenges and solutions to ultra-high-throughput screening assay miniaturization: submicroliter fluid handling" DDT, 20000, vol. 5, No. 12 (Suppl.) pp. S84-S91.

McGrath et al., "Simultaneous measurements of Actin Filament Turnover, filament Fraction, and Monomer Diffusion in Endothelial Cells" Biophysical Journal, Oct. 1998, vol. 75, pp. 2070-2078.

Olechno et al., "Improving IC50 Results with Acoustic Droplet Ejection" JALA, Aug. 2006, 11:240-246.

Olechno et al., "Contact-free, direct dilution minimizes compound loss in dose-response experiments" Labcyte, Inc., Sunnyvale, CA, 1 page.

Lee et al., "2-layer based microfluidic concentration generator by hybrid serial and volumetric dilutions" Biomed Microdevices, 2010, 12:297-309.

MacDonald et al., "Correction of fluorescence inner filter effects and the partitioning of pyrene to dissolved organic carbon" Analytica Chimica Acta, 1997, 338:155-162.

Liu et al., "Use of a Fluorescence Plate Reader for Measuring Kinetic Parameters with Inner Filter Effect Correction" Analytical Biochemistry, 1999, 267:331-335.

Fanget et al., "Correction of Inner Filter Effect in Mirror Coating Cells for Trace Level Fluorescence Measurements" Anal. Chem., 2003, 75:2790-2795.

Kubista et al., "Experimental Correction for the Inner-filter Effect in Fluorescence Spectra" Analyst, Mar. 1994, vol. 119, 417-419.

Lakowicz, J.R., Book Review. "Principles of Fluorescence Spectroscopy", Third Edition, J. Biomedical Optics, Mar./Apr. 2008, vol. 13(2), pp. 1-2.

Gu et al., "Improvement of Inner Filter Effect Correction Based on Determination of Effective Geometric Parameters Using a Conventional Fluorimeter", Anal. Chem., 2009, 81:420-426.

Rao, B.G. "Recent Developments in the Design of Specific Matrix Metalloproteinase Inhibitors aided by Structural and Computational Studies", Current Pharmaceutical Design, 2005, 11:295-322.

Asahi et al., "Role for Matrix Metalloproteinase 9 After Focal Cerebral Ischemia: Effects of Gene Knockout and Enzyme Inhibition With BB-94", Journal of Cerebral Blood Flow and Metabolism, 2000, 20:1681-1689.

Rasmussen et al., "Matrix Metalloproteinase Inhibition as a Novel Anticancer Strategy: A Review with Special Focus on Batimastat and Marimastat" Pharmacol. Ther., 1997, vol. 75, No. 1, pp. 69-75.

Abate et al., "High-throughput injection with microfluidics using picoinjectors" PINAS, Nov. 9, 2010, vol. 107, No. 45, pp. 19163-19166.

Jambovane et al., "Determination of Kinetic Parameters, Km and Kcat, with a Single Experiment on a Chip", Anal. Chem, 2009, 81:3239-3245.

SYSTEM AND METHODS OF LOG-SCALE CONCENTRATION GRADIENTS

FIELD OF THE INVENTION

The present invention relates to the field of integrated microfluidic systems. More specifically, the present invention relates to the field of microfluidic systems for sample handling and drug discovery.

BACKGROUND OF THE INVENTION

In the process of drug discovery, quantitative characterization of inhibitory potencies of all the potential drug candidates is often needed to figure out the best candidate. For comparing potential drug candidates, an outcome of curve fitting of a sigmoidal curve to the dose response data or the value of half maximal inhibitory concentration, $IC_{50}$, is able to be used. Inhibitors are small molecules that impede the substrate molecules from reaching or binding to the enzyme active sites. Half of today's drugs are inhibitors. In dose response analysis, the use of a wide concentration range is important because the dose response is represented by a Maltusian-type differential equation. The solution of the equation is logarithmic type. Recently, the importance of a log scale for a drug response analysis, based on thermodynamical basis, has been reported. The drug response is directly proportional to the log of the drug concentration, which is expressed as $\mu = RT \ln[a]$, where $\mu$ is chemical potential or response of the drug, [a] is an activity or concentration of the drug, R is a constant number, and T is a temperature (e.g. absolute temperature). Hence, drug concentrations that are equally spaced using a logarithmic scale instead of a linear scale are selected.

Conventionally, serial dilutions with test tubes, vials, and micro-plates are routinely used for the preparation of a concentration gradient in the determination of $IC_{50}$. However, it is well known that the serial dilution method introduces ample errors through pipetting that directly affect the precision of each dilution ratio. The error in each step of serial dilution is able to lead to significant errors after several steps of serial dilution. This is able to affect the evaluation of $IC_{50}$ values of drug candidates and their realistic comparisons. Therefore, direct dilution of drugs has been recommended for the evaluation of $IC_{50}$.

Conventional approaches are available for handling samples with direct dilution by using individually addressable piezo dispenser and acoustic droplet ejection through a vibrating piezo transducer. These involve the use of conventional micro plates for hosting reagents and letting the reactions to occur. These conventional methods still need milliliters or liters of reaction solutions.

SUMMARY OF THE INVENTION

Devices for and methods of analyzing dose response of enzyme inhibitors are provided. The devices and methods use an integrated microfluidic system that has the capability of realizing a wide range of accurate dilutions in a logarithmic way through semi-direct dilution of samples inside a chip.

In a first aspect, a method of performing quantitative drug information analysis comprises mixing a first fluid and a second fluid to form a third fluid on a microfluidic device, receiving the drug information from the third fluid, and performing analysis on the drug information. In some embodiments, the first fluid, the second fluid, the third fluid or a combination thereof comprises a volume in nanoliter scale. In other embodiments, the microfluidic device comprises a microfluidic chip. In some other embodiments, the second fluid dilutes the first fluid. In some embodiments, the first fluid comprises a drug, a growth factor, a growth stimulant, or a combination thereof. In other embodiments, the drug comprises an inhibitor, an enzyme, or a chemical having a therapeutical effect. In some other embodiments, the second fluid comprises a buffer solution. In some embodiments, the drug information comprises dose response data. In other embodiments, the analysis comprises determining a drug response. In some other embodiments, the drug response is proportional to the log of a drug concentration in the third fluid. In some other embodiments, the drug response is received from a bacterial cell, a fungus, a mammalian cell, or a combination thereof.

In a second aspect, a device for dose response analysis comprises a first fluid source on a microfluidic chip, wherein the first fluid source comprises a drug, a second fluid source on the microfluidic chip, a mixing area on the microfluidic chip fluidically coupling with the first and the second fluidic source, and a detection area coupling with the mixing area for drug information detection. In some embodiments, the second fluid source comprises a buffer solution. In other embodiments, the first fluid source comprises an inhibitor, an enzyme, or a chemical having a therapeutical effect. In some other embodiments, the microfluidic chip is able to mixing a first amount of fluid from the first fluid source and a second amount of fluid from the second fluid source making a first drug solution with a first concentration and a second drug solution with a second concentration, wherein the first concentration and the second concentration are logarithmically related. In some embodiments, the first fluid source, the second fluid, or both are able to generate a solution in a volume equal or smaller than micro-liter. In other embodiments, the volume is nano-liter. In some other embodiments, the volume is pico-liter. In some embodiments, the drug information is received from a bacterial cell, a fungus, a mammalian cell, or a combination thereof. In other embodiments, the device further comprises a temperature control system capable of controlling the kinetics of a reaction. In some other embodiments, the device further comprises a humidity control system capable of preventing evaporation. In some embodiments, the device is able to provide accurate reaction kinetics.

In a third aspect, a method of logistic dose response analysis comprises diluting a drug solution into a sample solution using a microfluidic device, detecting drug information from the sample solution, and determining a drug response using the drug information. In some embodiments, the diluting comprises direct or semi-direct dilution. In other embodiments, the drug response comprises $IC_{50}$ (half maximal inhibitory concentration), $EC_{50}$ (half maximal effective concentration), $LD_{50}$ (median lethal dose), $LCt_{50}$ (Lethal Concentration & Time), or $LC_{50}$ (lethal Concentration, 50%). In some other embodiments, detecting drug information comprises detecting a fluorescent emission. In some embodiments, the sample solution comprises a volume equal or smaller than micro-liter. In other embodiments, the microfluidic device comprises multiple fluidic sources. In some other embodiments, the microfluidic device couples with a controlling device, wherein the controlling device capable of transporting a movement of one or more fluids on the microfluidic device. In some embodiments, determining a drug response is performed on a computing device. In some other embodiments, the drug response is received from a bacterial cell, a fungus, a mammalian cell, or a combination thereof.

In a fourth aspect, a method of performing quantitative drug information analysis comprises mixing a first fluid and a second fluid to form a third fluid on a microfluidic device, detecting the drug information from the third fluid, and performing analysis on the drug information. In some embodiments, the method further comprises an optical detection system to detect the drug information. In other embodiments, the method further comprises an electrochemical detection system to detect the drug information.

In a fifth aspect, a device for preparing a fluid sample comprises a first fluid source on a microfluidic chip, wherein the first fluid source comprises a first fluid, a second fluid source on the microfluidic chip, wherein the second fluid source comprises a second fluid, and a mixing area on the microfluidic chip fluidically coupling with the first and the second fluid source capable of making multiple concentrations. In some embodiments, the second fluid source comprises a buffer solution. In some other embodiments, the microfluidic chip is able to mixing a first amount of fluid from the first fluid source and a second amount of fluid from the second fluid source making a first sample solution with a first concentration and a second sample solution with a second concentration, wherein the first concentration and the second concentration are logarithmically related. In some embodiments, the first fluid source, the second fluid source, or both are able to generate a solution in a volume equal or smaller than micro-liter. In some other embodiments, the volume is nano-liter. In some embodiments, the volume is pico-liter.

DETAILED DESCRIPTION OF THE PREFERRED EMBODIMENT

An integrated microfluidic system/device disclosed herein is able to be used for a drug response analysis. In some embodiments, dose response curves and determined $IC_{50}$ values of three inhibitors, marimastat, batimastat and CP471474 for matrix metalloproteases-9 (MMP-9) and MMP substrate III are measured by conducting a series of dose response reactions in logarithmic concentration gradients with nanoliters of drug or inhibitor samples.

Figure 1:
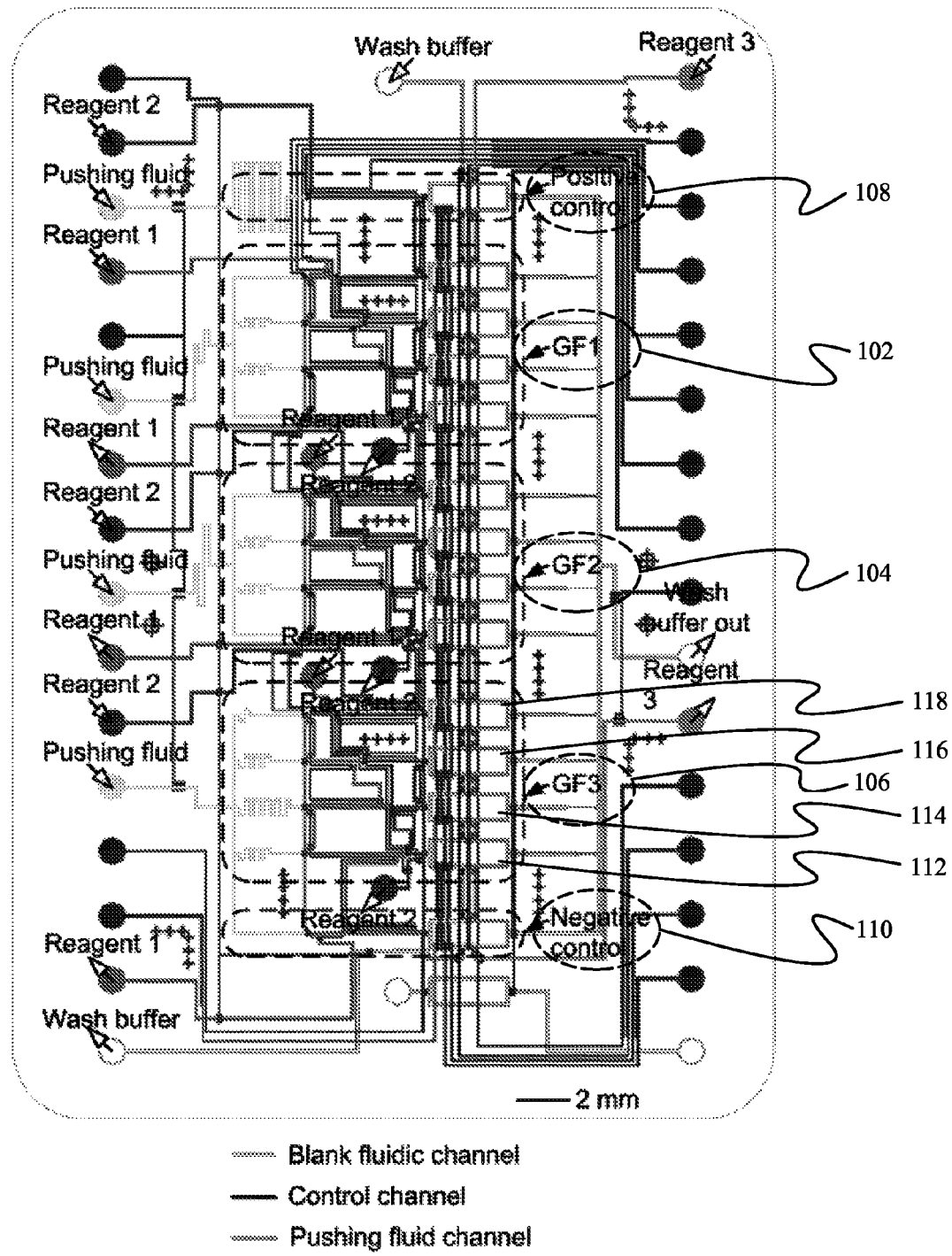
FIG. 1 illustrates a design of a microfluidic chip in accordance with some embodiments.

FIG. 1 illustrates a design of a microfluidic chip 100 in accordance with some embodiments. The chip 100 is able to be designed and fabricated using a multilayer soft lithography technique. The chip is able to compose of three gradient formers (GF) 102, 104, and 106. Each GF is able to contain 4 microfluidic processors. For example, the GF 106 comprises processors 112, 114, 116, and 118. Each microfluidic processor is able to be a subunit of GF for metering, incubation, mixing and optical detection. These processors, GF1, GF2, and GF3, are able to measure two reagents in the ratios of 7.5:2.5, 5.0:5.0, 2.5:7.5 and 1.0:9.0. A person of ordinary skill in the art will appreciate that any ratios of the two reagents are applicable. In some embodiments, the chip includes two separated processors 108 and 110 for positive and negative controls. For example, a reagent of 1×, 10×, and 100× is able to be introduced into the three GFs along with 1000× for positive control and a blank buffer for negative. Therefore, a concentration range of 0 to 1000×, in logarithmic scale, is able to be generated in a single experiment.

To determine the kinetic parameters, KM and kcat, the initial velocities of the individual reactions are able to be curve-fitted with the Michaelis-Menten equation using the enzyme kinetics module of Sigmaplot software (Systat software Inc.). For $IC_{50}$ values with standard error, and 95% confidence interval, the four parameter nonlinear-logistic-regression model available to the inhibition data are curve-fitted. The four parameter model is of the form as shown in the equation (1) below.

$$\% I = I_{min} + \frac{I_{max} - I_{min}}{1 + ([I]/IC_{50})^{-h}} \quad (1)$$

Where, $IC_{50}$ refers to median point of the concentration-response plot; [I] represents the concentration of inhibitor; h is the Hill coefficient or Hill slope, which means the steepness of dose-response plot; %I designates percentage inhibiting potency, including minimum and maximum.

In some embodiments, each GF has two separate inlets for inhibitor (reagent 1) and buffer (reagent 2). In some embodiments, three identical GFs are able to allow conducting three repetitive experiments with fixed concentration range if an inhibitor and reagent with the same concentrations are fed. For example, if 10× inhibitor (reagent 1) and 1× working buffer (reagent 2) are introduced, final inhibitor concentrations of 1×, 2.5×, 5× and 7.5× are able to be created. A wider concentration range is able to be derived from the device by feeding different concentrations of inhibitor (reagent 1) in the three GFs, and by keeping the same concentration of working buffer. If 10× inhibitor is fed to the first GF1, 100× to the GF2, then 1000× to the GF3, the effective concentrations in each GF will respectively be 1, 2.5, 5, 7.5×, for GF1; 10, 25, 50, 75×, for GF2; 100, 250, 500, 750×, for GF3. Here the negative and positive control processors are able to generate 0 and 1000× concentrations. Therefore, by introducing the three concentrations of inhibitor and buffer, meaningful logarithmic concentrations for dose response are generated such as 0, 1, 2.5, 5, 7.5, 10, 25, 50, 75, 100, 250, 500, 750 and 1000× by the device disclosed herein in semi-direct dilution. However, the concentration range is able to be easily increased by changing the input concentration of the inhibitor while keeping buffer the same. In some experiments, a concentration range from 1× to 4000× has been created by using 1×, 50× and 4000× of inhibitors for the three GFs. The individual microfluidic processors are able to have nano-liters scale volume. Hence large amount of samples are able to be saved during dose response analysis in comparison to the large amount of reagent volumes used in conventional methods.

Figure 2A:
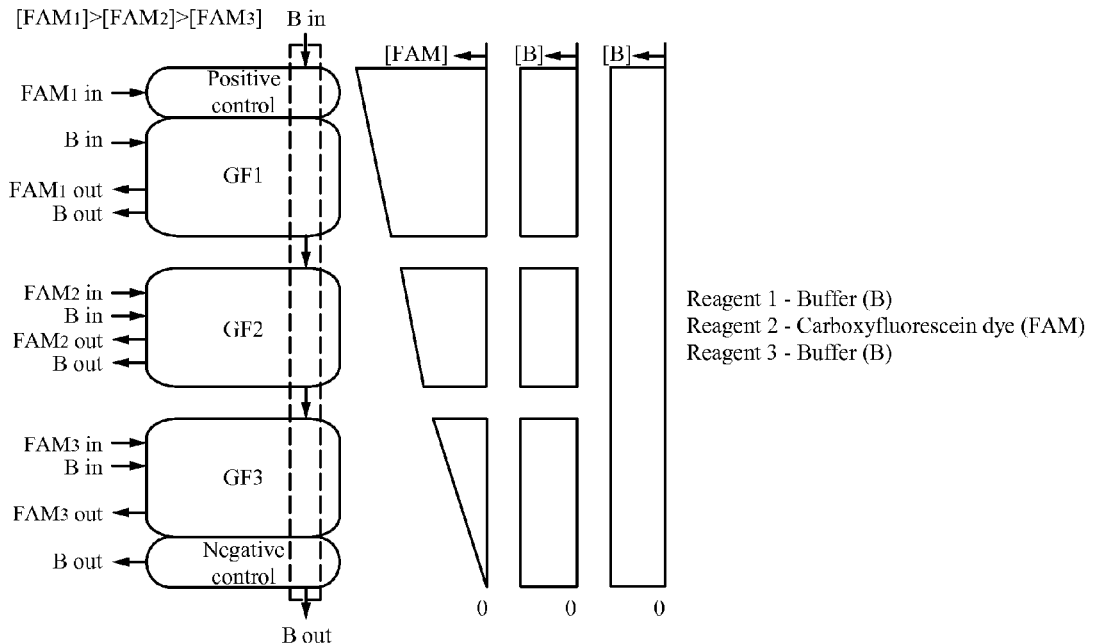
FIG. 2A illustrates a method of generating standard curve of FAM gradient using the microfluidic chip in accordance with some embodiments.

FIG. 2A illustrates a method of generating standard curve of FAM gradient using the microfluidic chip in accordance with some embodiments. The method disclosed herein is able to generate a concentration gradient of carboxyfluorescein (FAM) in the ratio of 1:1,000. A person of ordinary skill in the art will appreciate that any other ratio is applicable. To generate this concentration gradient, FAM is introduced with three concentrations, 0.05 μM, 0.5 μM and 5 μM, into the reagent input ports of GF1 102, GF2 104, and GF3 106 (FIG. 1), respectively. The reaction buffer with a fixed concentration is also introduced to dilution buffer input ports of GF1, GF2 and GF3. Therefore, a concentration gradient range of 0.0025 μM to 2.5 μM is able to be generated in the 13 microfluidic processors.

Figure 3:
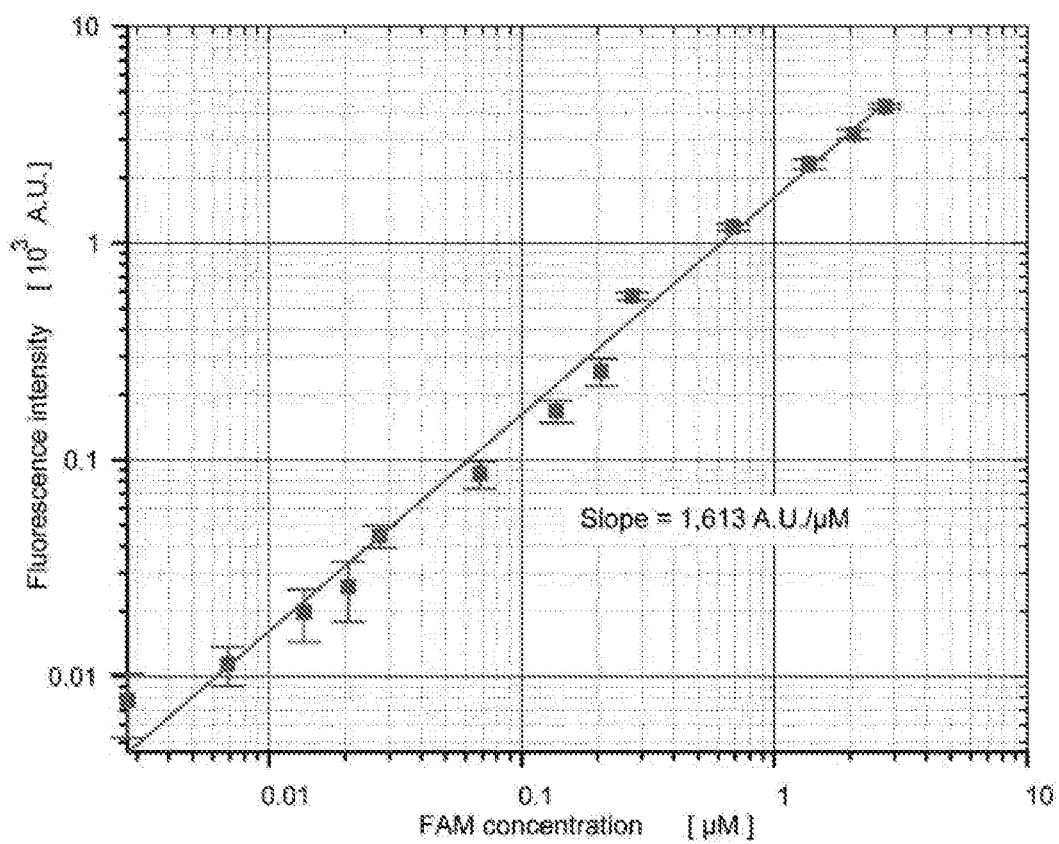
FIG. 3 illustrates a log-log scale standard curve for FAM established from 3 independent experiments conducted with logarithmic gradients on a chip in accordance with some embodiments.

FIG. 3 illustrates a log-log scale standard curve for FAM established from 3 independent experiments conducted with logarithmic gradients on a chip in accordance with some embodiments. In the standard curve, a linear relationship is observed, with a slope of 1,613 AU/μM, between concentration of FAM and the corresponding fluorescence intensity.

The half maximal inhibitory concentration, $IC_{50}$ is able to be influenced by analysis conditions, such as pH, ionic strength, and substrate concentration. Among these factors the most dominant factor influencing $IC_{50}$ value is able to be the [S]/KM ratio. For the determination of $IC_{50}$ value from a logistic-dose response curve, the selection of substrate concentration equal to the value of KM is recommended. Therefore, the KM value for matrix metalloproteinase-9 (MMP-9) is first determined before measurement of the inhibiting potency of the inhibitors.

Figure 2B:
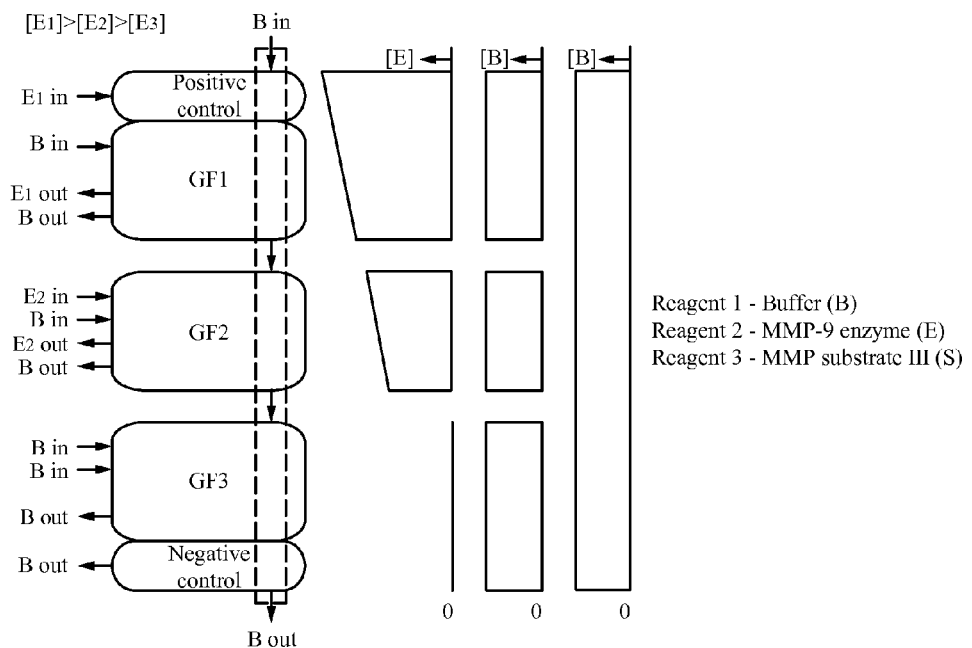
FIG. 2B illustrates a method of generating enzyme gradient using the microfluidic chip in accordance with some embodiments.

FIG. 2B illustrates a method of generating enzyme gradient using the microfluidic chip in accordance with some embodiments. For the determination of reliable values of $IC_{50}$ and KM, selecting the concentration of enzyme that shows linear reaction progress is important. To decide the enzyme concentration only part of the microfluidic chip is used. In some examples, enzyme solutions of 2 nM and 20 nM are introduced to GF1 102 and GF2 104 (FIG. 1) to form an enzyme concentration gradient in the range of 0.1 nM~10 nM (1:100). (the group GF3 106 (FIG. 1) is not used in this example because concentration of enzyme over 10 nM is not needed.)

Figure 4:
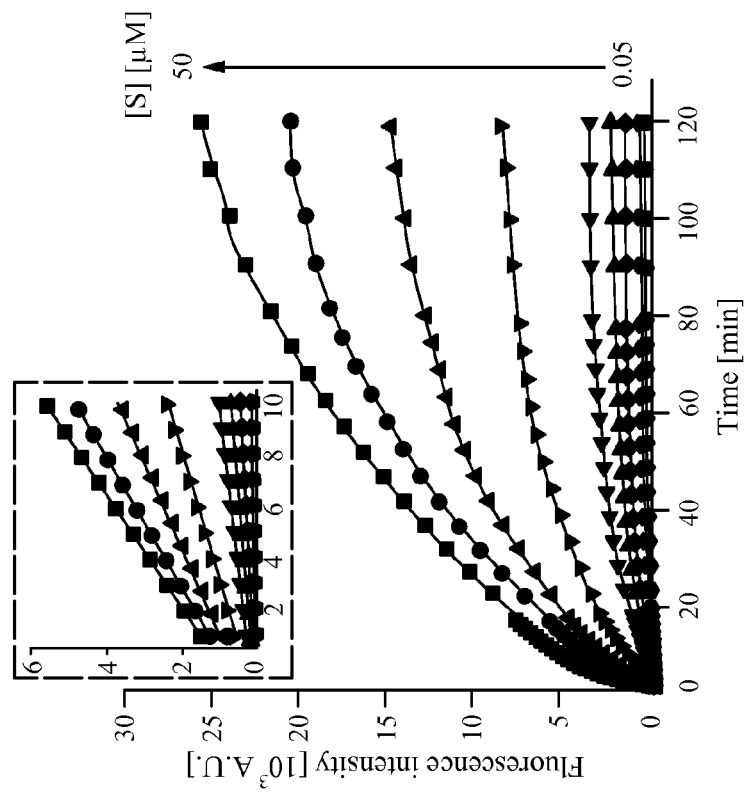
FIG. 4 illustrates results of generating concentration gradient using the on-chip method in accordance with some embodiments.
Figure 4:
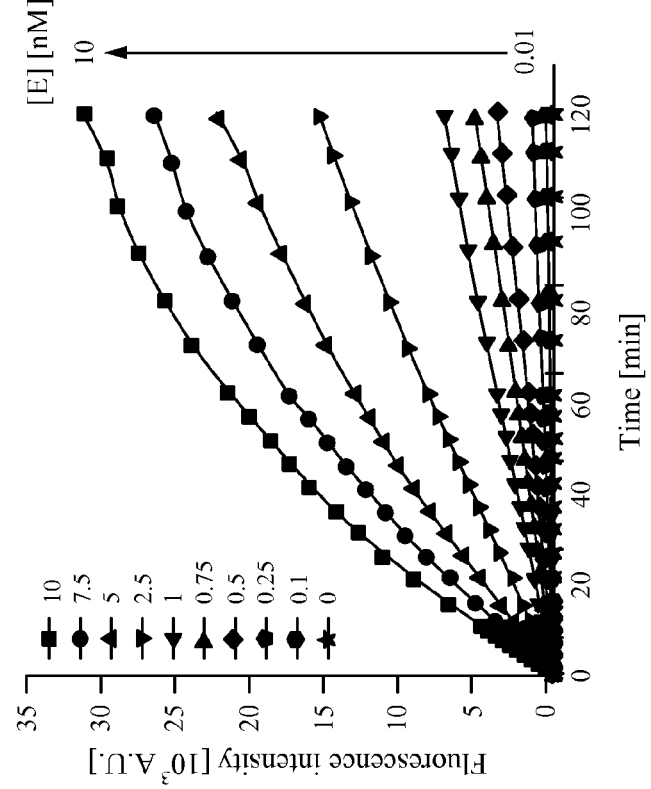

FIG. 4 illustrates results of generating concentration gradient using the on-chip method in accordance with some embodiments. When 50 μM of MMP substrate III is used, it is observed that even with a measuring time of 120 minutes, the kinetic reaction does not reach the plateau for enzyme concentrations as high as 10 nM. Therefore, 10 nM of enzyme concentration is chosen to determine reaction velocities for further kinetic analysis.

Figure 2C:
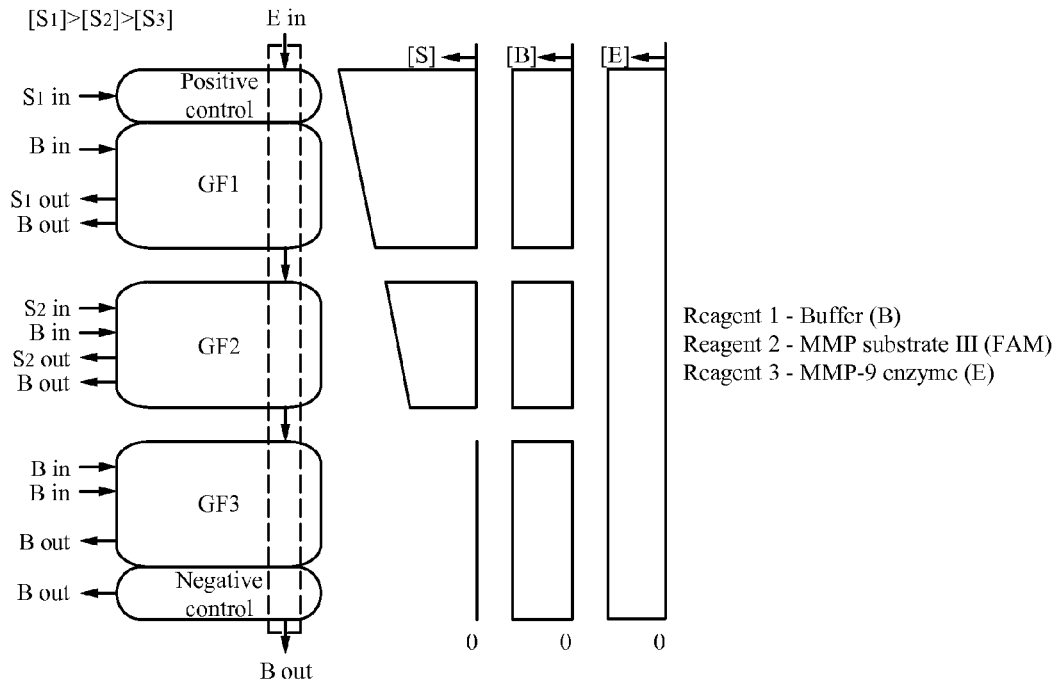
FIG. 2C illustrates a method of generating substrate gradient using the microfluidic chip in accordance with some embodiments.

FIG. 2C illustrates a method of generating substrate gradient using the microfluidic chip in accordance with some embodiments. To determine the kinetic parameters, KM and kcat, of MMP-9, 100 μM substrate for GF1 102 and 10 μM for GF2 104 (FIG. 1) are introduced, respectively, along with the dilution buffer and 20 nM MMP-9 enzyme. The GF3 106 (FIG. 1) is not used for generating concentration gradient. As a result, 1 μM~100 μM (1:100) of substrate concentration gradient is formed on the chip in the metering channels. After mixing the metered substrate and enzyme into the reactor mixer, the substrate concentration gradient becomes 0.5 μM~50 μM in 9 processors (GF1, GF2 and positive control).

FIG. 4 illustrates the results of 9 independent enzyme reactions in accordance with some embodiments. From this plot, it is observed that the rate of reaction increased with the increase of substrate concentration in the 9 microfluidic processors. The reaction rates are linear up to 10 minutes. Therefore, the initial reaction velocity is calculated from these linear parts of the progress curves.

Figure 5A:
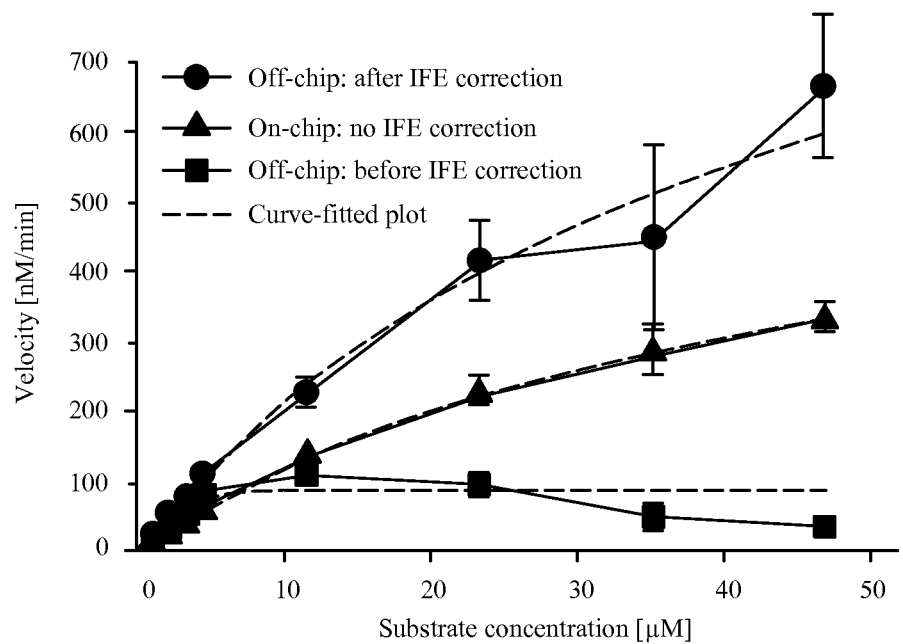
FIGS. 5A and 5B illustrate a method of determining enzyme kinetic parameters in accordance with some embodiments.
Figure 5B:
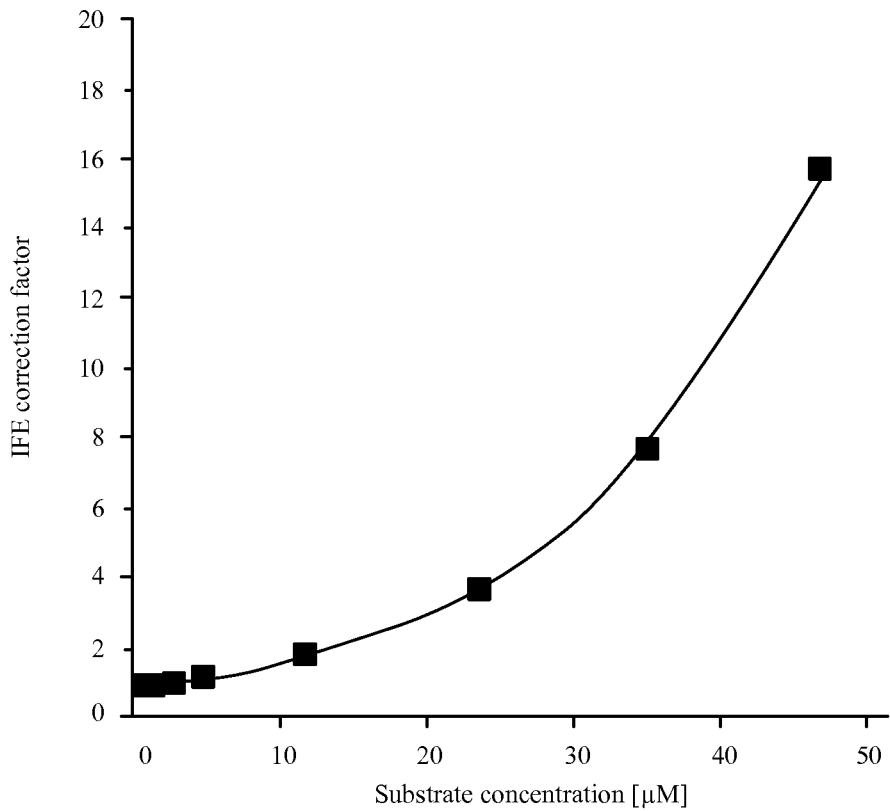

FIGS. 5A and 5B illustrate a method of determining enzyme kinetic parameters in accordance with some embodiments. As shown in FIG. 5A, a Michaelis-Menten plot is prepared from the initial velocity data of three repetitive experiments. Applying nonlinear curve-fitting to the plot, KM and kcat are determined from the on-chip experiments and the respective values are 53.4±5.2 μM and 55.8±4.1/min. For comparison, three off-chip experiments are conducted and the values of KM and kcat are 41.2±4.7 μM and 84.9±0.9/min. The deviation between on-chip and off-chip KM values is 25.8% whereas kcat is 41.3%. This discrepancy is able to be attributed to the characteristics of fluorescence detection that is relevant especially at higher substrate concentration with large optical path length. Unlike absorbance based measurement, the fluorescence detection experiences significant loss of fluorescence intensity at higher substrate concentrations, known as the inner filter effect. The correction factors are used to compensate for the loss of florescence intensity.

FIG. 5B shows that the correction factors exponentially increases with the increase of substrate concentrations. On the other hand, in some of the chip experiments, negligible saturation of fluorescence intensity under the same substrate concentration range is observed. These differences are believed due to a different length of optical path for on-chip, ~10 μm, and off-chip, ~5 mm, experiments. In addition to the fact that an enzyme is a biological sample with variable properties.

Figure 2D:
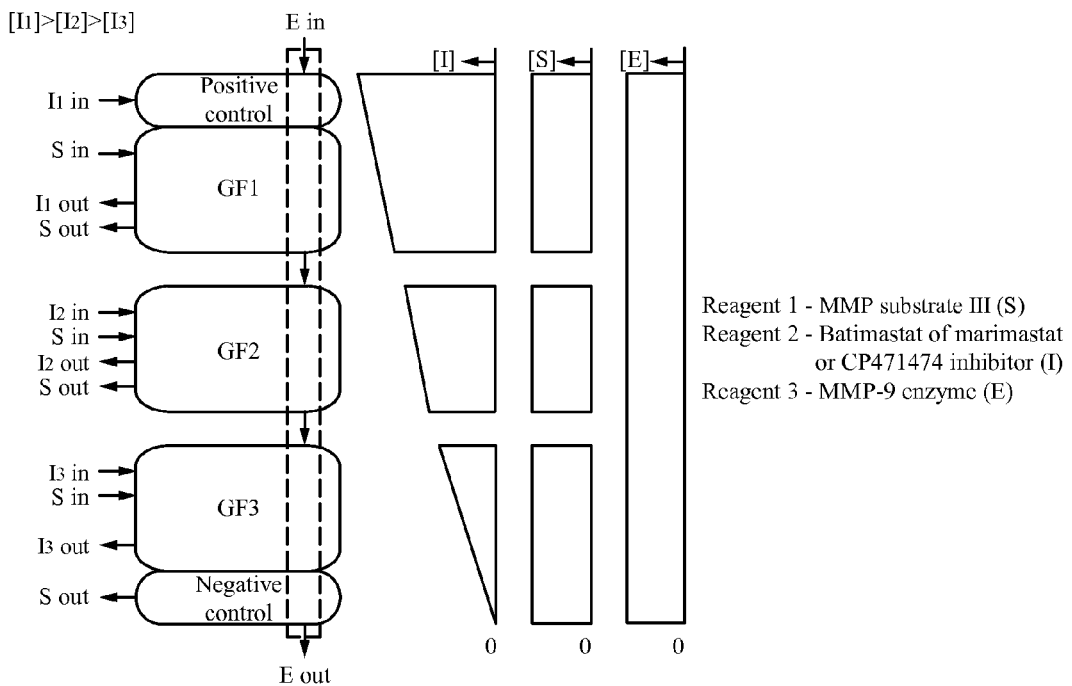
FIG. 2D illustrates a method of generating an inhibitor dosage response analysis using the microfluidic chip in accordance with some embodiments.

FIG. 2D illustrates a method of generating an inhibitor dosage response analysis using the microfluidic chip in accordance with some embodiments. To show the ability of the device to generate a logarithmic concentration gradient and the functionality of the device to conduct logistic dose response studies, the $IC_{50}$ values of three inhibitors, marimastat, batimastat and CP417474 are determined, of the MMP-9 enzyme from their corresponding logistic dose response plots. An inhibitor concentration range of 0.063 nM~250 nM (1:4000) is created on the chip in the 14 reactors. Note that, all the 14 reactors are used considering the requirement of a wider concentration range of inhibitors (FIG. 2D), 22.15 μM of substrate and 5 nM of enzyme are used, respectively.

Figure 6:
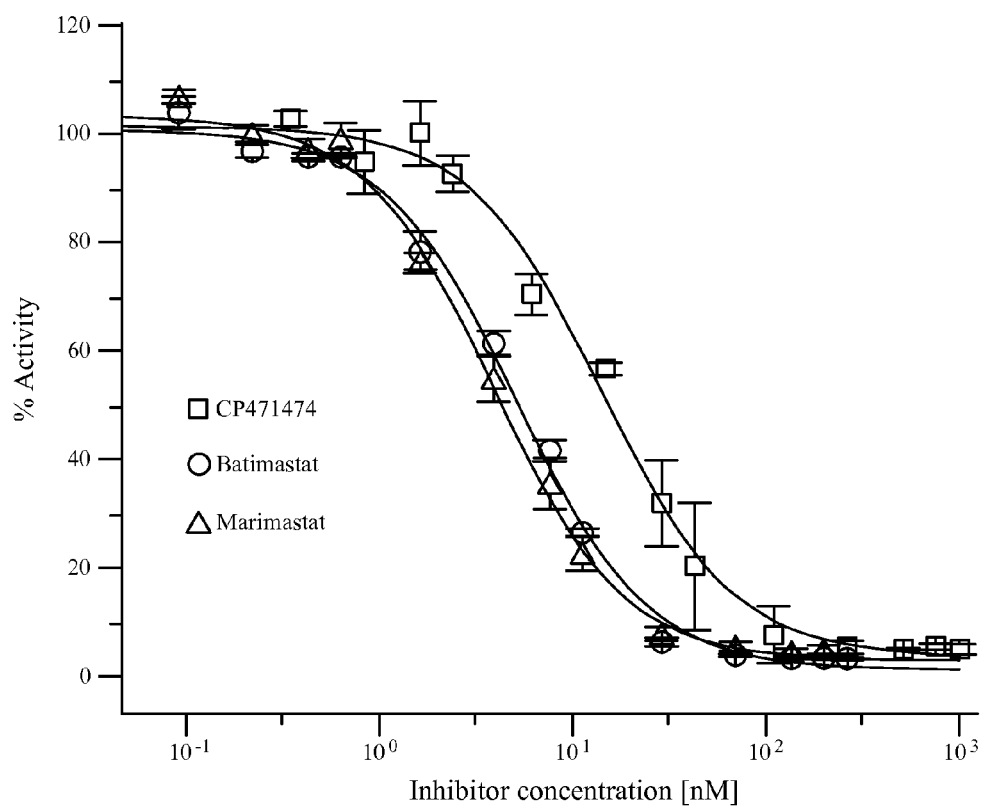
FIG. 6 illustrates dose response plots for the 3 inhibitors, marimastat, batimastat and CP417474 in accordance with some embodiments.

FIG. 6 illustrates dose response plots for the 3 inhibitors, marimastat, batimastat and CP417474 in accordance with some embodiments. From these plots, the $IC_{50}$ values for marimastat, batimastat and CP417474 are 3.2±0.2 nM, 4.1±0.2 nM and 11.9±1.0 nM, respectively. The respective $IC_{50}$ values from the off-chip experiment are 3.1±0.1 nM (marimastat), 3.5±0.3 nM (batimasat) and 14.9±0.9 nM (CP417474). Through the comparison of the results from on-chip experiment and off-chip experiment, it is observed the deviation of 3.2%, 17% and 20% in the $IC_{50}$ values of marimastat, batimastat, and CP417474 inhibiters, respectively. From some literature, the reported $IC_{50}$ values for marimastat and batimastat are 3 nM and 3-4 nM, respectively. These deviations in the values of $IC_{50}$ are acceptable, considering enzyme as a biological sample with variable properties. Therefore, the microfluidic chip in accordance with some embodiments is able to provide reliable determination of $IC_{50}$ values of inhibitors with the automation of sample preparation, gradient generation, mixing, incubation and optical detection.

Figure 7:
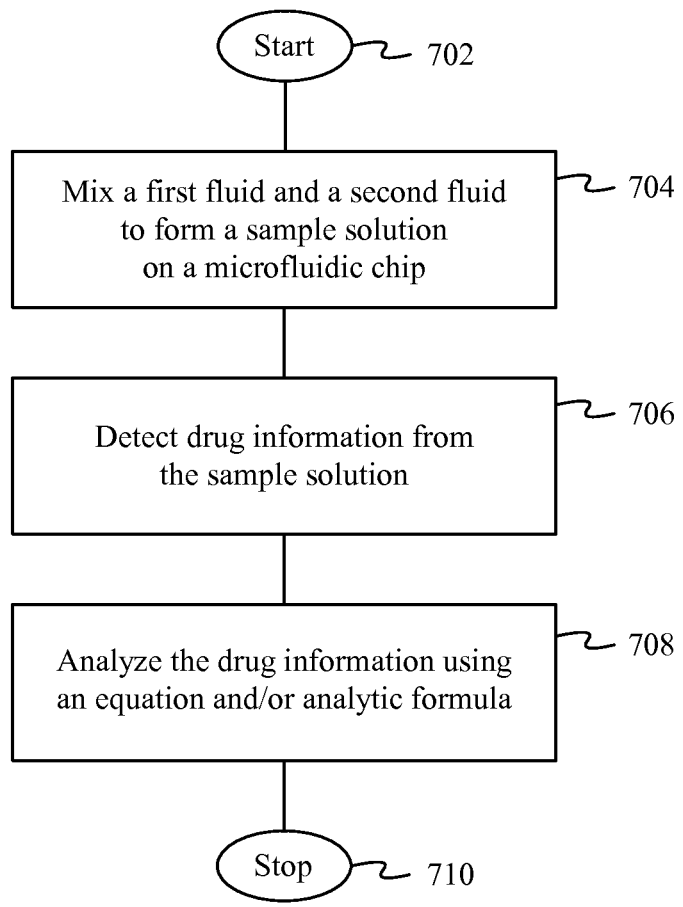
FIG. 7 illustrates a flow chart showing a method of generating a dosage response analysis using the microfluidic chip in accordance with some embodiments.

FIG. 7 illustrates a flow chart showing a method 700 of generating a dosage response analysis using the microfluidic chip in accordance with some embodiments. The method 700 is able to start from a step 702. The method 700 is able to be performed on the microfluidic chip described in the FIG. 1 and its associated descriptions. At step 704, a first fluid and a second fluid are mixed to form a sample solution. The first fluid and the second fluid are able to respectively come from the first fluid source and the second fluid source on the microfluidic chip described above. The first and/or the second fluid are able to have a volume in a nano-liter range. The sample solution is also able to have a volume in the nano-liter range.

At step 706, drug information is detected from the sample solution. The detection is able to be performed using any chemical, physical, and/or biological methods including light emitting properties, chemiluminescent, fluorescent, phosphorescent, and electrical. A person of ordinary skill in the art will appreciate that any analytical methods are able to be used. At step 708, the drug information is analyzed using equations and/or analytic formula. The equations and the analytic formula are able to be any medical equations, statistic formula, mathematical formula, analytical methods used for drug analysis. For example, a drug response equation, $\mu=RT \ln[a]$, is used as an analytic tool. The drug response is directly proportional to the log of the drug concentration, where $\mu$ is chemical potential or response of the drug and $[a]$ is an activity or concentration of the drug. The microfluidic chip disclosed herein is able to prepare samples with different concentrations that fits the need of the analysis. For example, a computer couples with the microfluidic chip is able to monitor, compute, and/or control every part of the microfluidic components on the microfluidic chip, so that samples with desired concentrations are able to be prepared, such as a first sample with a first drug concentration having a logarithmic relationship in its concentration with a second sample with a second drug concentration. A person of ordinary skill in the art will appreciate that samples with same concentrations or different concentrations are able to be prepared using the microfluidic chip described above. The samples with same concentrations are able to be used to verify the accuracy and/or repetitivability of the experiments and the results of the analysis. The samples with different concentrations are able to be used to explore and verify the data curve/line of a formula and/or an equation. A person of ordinary skill in the art will appreciate that any numbers of drugs and any types of drugs are able to be studied on the microfluidic chip disclosed herein. The term "drug" is able to include any chemicals that are able to be used for an illness, sickness, injury treatment and/or healing. The term "drug" is able to be any chemicals or physical properties (such as electricity) that has a therapeutical effect, a biologic effect, a chemical effect, a combination thereof, such as an enzyme and an inhibitor. The method 700 is able to stop at step 710.

The device in accordance with some embodiments is able to be used for the concentration-response analysis of reagents where a logarithmic scale concentration gradient is required. The device is able to be used for various applications where log-scale gradient with flexibility of concentration range is needed.

The system in accordance with some embodiments is able to be used for the evaluation of $EC_{50}$ (half maximal effective concentration), $LD_{50}$ (median lethal dose), $LCt_{50}$ (Lethal Concentration & Time), and $LC_{50}$ (lethal Concentration, 50%) by using microbial cells or animal cells or for conducting cell cytotoxicity assays. A person of ordinary skill in the art will appreciate that the devices, systems, procedures disclosed herein are able to be used for any medicinal, chemical, reagent analysis in nano and/or micro liter scale. These dose-response or cytotoxicity experiments are able to be conducted by feeding the cells to the constant volume part of the mixer and forming the gradient of inhibitors or reagent, for which the toxicity limit is to be determined, in group of reactors.

In conclusion, an approach of logarithmic concentration gradient generation is demonstrated with an integrated microfluidic chip that has semi-direct dilution capability of reagents in addition to metering and mixing of reagents with 14 parallel micro processors. It has been shown that the concentration range from 1:0 to 1:4000 of two reagents is able to be easily realized on the system disclosed herein. In some of the demonstrative experiments, $IC_{50}$ values of three inhibitors (marimastat, batimastat and CP417474 for MMP-9 enzyme) are successfully determined from the corresponding logistic dose response plots of each inhibitor with a single on chip experiment. Using the system disclosed herein, the inner filter effect is successfully avoided that is common with high substrate concentrations with conventional cuvettes. The devices disclosed herein are able to be a useful tool for pharmaceutical sciences especially for the evaluation of $IC_{50}$ of various compounds through systematic handling of reagents in nano-liter scale.

Experimental Section

The substrate QXLTM520-Pro-Leu-Gly-Cys-(Me)-His-Ala-D-Arg-Lys-(5-carboxy-fluorescein)-NH2 (AnaSpec Inc), internally quenched peptide matrix of matrix metalloproteinases-9 (MMP-9) is used for the enzyme reaction. This substrate releases fluorescent signals through dissociation of the quencher (QXLTM520) and carboxyfluorescein (FAM), fluorophore, via proteolytic cleavage by enzymatic reaction. MMP-9 is known to directly or indirectly influences human diseases, such as infiltration and metastasis of cancer cell and arthritis, hence, MMP-9 is one of the major targets for development of anticancer drugs. For establishing a standard curve, reference dye, FAM-Pro-Leu-OH is used. The excitation and emission wavelengths for FAM are 480 nm and 520 nm, respectively. According to the enzyme reaction types, 50 nM, 10 nM, and 5 nM of MMP-9 are separately dissolved into the reaction buffer (TCNBT; 50 mM Tris, 10 mM $CaCl_2$, 150 mM NaCl, 0.05% Brij-35, 0.05% Tween-20 and 0.1% BSA at pH 7.5). For the substrate of MMP, a stock solution is prepared as 100 μM in TCNBT buffer. Inhibitors of MMP-9, e.g. marimastat and batimastat (Tocric bioscience Co.) are dissolved into DMSO in 10 mM of stock solution. Prepared reagents are stored at −20° C. until dilution with TCNBT buffer for experiment.

The type of reagents, its concentration and resultant concentration ranges enabling gradient for each experiment are summarized in Table 1.

TABLE 1

Compositions and concentrations of reagents introduced into an integrated microfluidic chip to produce a logarithmic gradient

| | | Reagents introduced into metering channels | | Constant reagent | Final concentrations of | Relative concentration |
|---|---|---|---|---|---|---|
| | | Reagent 1[a] | Reagent 2 | Reagent 3 | metered reagents | ranges[b] |
| [FAM] gradient [nM] | GF1 | 5000 | buffer | buffer | 2,500.00~250.00 | 1-1,000 |
| | GF2 | 500 | | | 187.50~25.00 | |
| | GF3 | 50 | | | 18.75~2.50 | |
| [E] gradient [nM] | GF1 | 20.0 | | 50 μM | 10.00~1.00 | 1-100 |
| | GF2 | 2.0 | | substrate in | 0.75~0.1 | |
| | GF3 | buffer | | buffer | 0 | |
| [S] gradient [μM] | GF1 | 100.0 | | 5 nM MMP-9 | 50.00~5.00 | |
| | GF2 | 10.0 | | in buffer | 3.75~0.5 | |
| | GF3 | buffer | | | 0 | |
| [Marimastat] [nM] | GF1 | 500.00[a] | 44.3 μm | 10 nM MMP-9 | 250~25 | 1-4,000 |
| | GF2 | 25.00[a] | substrate in | in buffer | 9.375~1.250 | |
| | GF3 | 1.25[a] | buffer | | 0.469~0.063 | |
| [CP 417474] [nM] | GF1 | 2,000.00[a] | | | 1,000~100 | |
| | GF2 | 100.00[a] | | | 37.5~5 | |
| | GF3 | 5.00[a] | | | 1.875~0.25 | |
| [Batimastat] [nM] | GF1 | 500.00a | | | 250~25 | |
| | GF2 | 25.00a | | | 9.375~1.250 | |
| | GF3 | 1.25 | | | 0.469~0.063 | |

[a]Inhibitor solutions included 44.3 μM substrate
[b]Ranges and concentrations are calculated with 13 microfluidic processors excluding a negative control The microfluidic chip disclosed herein is able to be used to prepare a wide range of concentrations of samples. For example, the concentrations prepared are able to be an arithmetic progression, a gradient relationship, and in a log relationship. A person of ordinary skill in the art appreciates that any other concentrations are able to be prepared using the devices and methods disclosed herein. In some embodiments, the microfluidic chip includes multiple processors for positive and negative controls. The various concentrations disclosed herein are able to be used to study the physical, chemical, and medicinal reactions of one or more study targets, such as a combinational method to study a drug's interactions with various other chemicals.

A person of ordinary skill in the art will appreciate that any ratios of the two reagents are applicable. In some embodiments, the chip includes two separated processors 108 and 110 for positive and negative controls. For example, a reagent of 1×, 10×, and 100× is able to be introduced into the three GFs along with 1000× for positive control and a blank buffer for negative. Therefore, a concentration range of 0 to 1000×, in logarithmic scale, is able to be generated in a single experiment.

To utilize the microfluidic chip for drug information analysis, formula and/or equations are able to be selected, samples are able to be prepared using the microfluidic chip, drug information are able to be detected from the sample, and results of the drug information are able to be analyzed.

In operation, the microfluidic chip is able to generate a first fluid from a first fluid source and a second fluid from a second fluid source, transport the first and the second fluids, mix/dilute/process the first and second fluid to become a third fluid, detect drug information from the third fluid, and analyze the result from the drug information detected. In some embodiments, the fluids comprise chemicals, drugs, enzymes, inhibitors, buffer solutions, or a combination thereof.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A device for dose response analysis comprising:
   a) a first fluid source on a microfluidic chip, wherein the first fluid source comprises a drug;
   b) a second fluid source on the microfluidic chip;
   c) a mixing area on the microfluidic chip fluidically coupling with the first and the second fluidic source;
   d) a logarithmic concentration former fluidically coupling with the first fluid source and the second fluid source; and
   e) a detection area coupling with the mixing area for drug information detection.

2. The device of claim 1, wherein the second fluid source comprises a control for controlling a buffer solution.

3. The device of claim 1, wherein the first fluid source comprises a control for controlling an inhibitor, an enzyme, or a chemical having a therapeutical effect.

4. The device of claim 1, wherein the microfluidic chip comprises a control to mix a first amount of fluid from the first fluid source and a second amount of fluid from the second fluid source making a first drug solution with a first concentration and a second drug solution with a second concentration, wherein the first concentration and the second concentration are logarithmically related.

5. The device of claim 1, wherein the first fluid source, the second fluid source, or both comprises a control to generate a solution in a volume equal or smaller than micro-liter.

6. The device of claim 5, wherein the volume is nano-liter.

7. The device of claim 5, wherein the volume is pico-liter.

8. The device of claim 1, wherein the drug information is received from a bacterial cell, a fungus, a mammalian cell, or a combination thereof.

9. The device of claim 1, further comprises a temperature control system capable of controlling the kinetics of a reaction or providing reaction kinetics.

10. The device of claim 1 further comprises a humidity control system capable of preventing evaporation.

11. A device for preparing a fluid sample comprising:
  a) a first fluid source on a microfluidic chip, wherein the first fluid source comprises a first fluid;
  b) a second fluid source on the microfluidic chip, wherein the second fluid source comprises a second fluid;
  c) a logarithmic concentration former fluidically coupling with the first fluid source and the second fluid source; and
  d) a mixing area on the microfluidic chip fluidically coupling with the first and the second fluidic source capable of making multiple concentrations.

12. The device of claim 11, wherein the second fluid source comprises a control for controlling a buffer solution.

13. The device of claim 11, wherein the microfluidic chip comprises a control to mix a first amount of fluid from the first fluid source and a second amount of fluid from the second fluid source making a first sample solution with a first concentration and a second sample solution with a second concentration, wherein the first concentration and the second concentration are logarithmically related.

14. The device of claim 11, wherein the first fluid source, the second fluid source, or both comprises a control to generate a solution in a volume equal or smaller than micro-liter.

15. The device of claim 14, wherein the volume is nano-liter.

16. The device of claim 14, wherein the volume is pico-liter.

* * * * *